US008435555B2

(12) United States Patent
Minter et al.

(10) Patent No.: US 8,435,555 B2
(45) Date of Patent: May 7, 2013

(54) SALT PRODUCT

(75) Inventors: Stephen John Minter, Derbyshire (GB); Sarah Maude, Nottinghamshire (GB)

(73) Assignee: Eminate Limited, Nottinghamshire (GB)

( * ) Notice: Subject to any disclaimer, the term of this patent is extended or adjusted under 35 U.S.C. 154(b) by 143 days.

(21) Appl. No.: 12/736,693

(22) PCT Filed: May 1, 2009

(86) PCT No.: PCT/GB2009/050458
§ 371 (c)(1),
(2), (4) Date: Dec. 6, 2010

(87) PCT Pub. No.: WO2009/133409
PCT Pub. Date: Nov. 5, 2009

(65) Prior Publication Data
US 2011/0098365 A1    Apr. 28, 2011

(30) Foreign Application Priority Data

May 1, 2008 (GB) .................................. 0807919.6

(51) Int. Cl.
*A61K 47/00* (2006.01)
*A61K 9/14* (2006.01)
*A61K 47/30* (2006.01)

(52) U.S. Cl.
USPC ........ 424/439; 424/489; 514/772.3; 514/777; 514/773; 514/778; 514/781

(58) Field of Classification Search .................. 424/489, 424/439; 514/772.3, 777, 773, 778, 781, 514/782
See application file for complete search history.

(56) References Cited

U.S. PATENT DOCUMENTS 2,539,012 A    1/1951    Diamond et al.
3,039,880 A    6/1962    Kawamura et al.
(Continued)

FOREIGN PATENT DOCUMENTS

DE    196 53 011    6/1998
EP    2 018 860    1/2009
(Continued)

OTHER PUBLICATIONS

Document filed in EPO on Nov. 30, 2011 in response to Examination Report dated May 20, 2011 in PCT International Application No. PCT/GB2009/050458 (EP Appln. No. 2009738439.0).

(Continued)

*Primary Examiner* — Blessing Fubara
(74) *Attorney, Agent, or Firm* — Nixon & Vanderhye P.C.

(57) ABSTRACT

A method of preparing a salt product comprises the steps of: (i) providing a mixture which comprises salt dissolved in a solvent, said mixture further containing an organic material that is solid under ambient temperature conditions; and (ii) atomising said mixture and evaporating said solvent to produce a salt product comprised of particles of salt incorporating said organic material. The organic material may be a polymer such as a carbohydrate (e.g. maltodextrin or Gum Arabic). Novel salt products are disclosed which comprise hollow particles having a shell formed for individual crystallites of salt. The salt product is useful as a seasoning for food and may be used in lower amounts than conventional salt to provide the same taste. Particular advantages are obtained in the baking of bread.

21 Claims, 9 Drawing Sheets

U.S. PATENT DOCUMENTS

| Patent | Kind | Date | Inventor |
|---|---|---|---|
| 3,082,154 | A | 3/1963 | Allan |
| 3,085,944 | A | 4/1963 | Valentine |
| 3,290,158 | A | 12/1966 | Treat |
| 3,556,718 | A | 1/1971 | Bachmann et al. |
| 3,760,941 | A | 9/1973 | Singewald et al. |
| 3,821,436 | A | 6/1974 | Fry |
| 3,855,397 | A | 12/1974 | Hoffman et al. |
| 4,460,563 | A | 7/1984 | Calanchi |
| 5,094,862 | A | 3/1992 | Bunick et al. |
| 5,098,723 | A | 3/1992 | DuBois et al. |
| 5,098,724 | A | 3/1992 | DuBois et al. |
| 5,482,720 | A | 1/1996 | Murphy et al. |
| 5,705,174 | A | 1/1998 | Benoff et al. |
| 6,090,419 | A | 7/2000 | Popplewell et al. |
| 6,140,598 | A | 10/2000 | Schoenert et al. |
| 6,143,211 | A | 11/2000 | Mathiowitz et al. |
| 6,235,224 | B1 | 5/2001 | Mathiowitz et al. |
| 2004/0213798 | A1 | 10/2004 | Maa et al. |
| 2005/0191396 | A1* | 9/2005 | Seltzer et al. ............... 426/548 |
| 2006/0286275 | A1 | 12/2006 | Salemme et al. |
| 2007/0059428 | A1 | 3/2007 | Chigurupati |
| 2008/0003344 | A1* | 1/2008 | Jensen et al. ............... 426/629 |
| 2008/0008790 | A1 | 1/2008 | Jensen et al. |

FOREIGN PATENT DOCUMENTS

| Country | Number | Date |
|---|---|---|
| GB | 713803 | 8/1954 |
| GB | 1361510 | 7/1974 |
| GB | 2440138 | 1/2008 |
| JP | 2006124234 | 5/2006 |
| KR | 2001000706 | 1/2001 |
| KR | 20020068706 | 8/2002 |
| WO | WO 96/22676 | 8/1996 |
| WO | WO 97/40704 | 11/1997 |
| WO | WO 98/07324 | 2/1998 |
| WO | 2008024820 | 2/2008 |
| WO | WO 2008/039533 | 4/2008 |

OTHER PUBLICATIONS

International Preliminary Report on Patentability for PCT/GB2009/050458, issued Nov. 2, 2010.

International Search Report for PCT/GB2009/050458, mailed Sep. 4, 2009.

* cited by examiner

EDAX images of bread, Green = Chlorine  Red = Sodium
High mag

Bread made with GA salt

Bread made with normal salt

SALT PRODUCT

This application is the U.S. national phase of International Application No. PCT/GB2009/050458 filed 1 May 2009, which designated the U.S. and claims priority to GB Application No. 0807919.6 filed 1 May 2008, the entire contents of each of which are hereby incorporated by reference.

The present invention relates to salt (i.e. sodium chloride) and relates more particularly to a method of producing a salt product as well as new forms of salt that are obtainable by the method. The invention is most particularly concerned with salt products which have a very small particle size (e.g. less than 100 microns) and which remain free-flowing even when stored under ambient conditions. The salt products are particularly useful for use as a seasoning in manufactured foodstuffs, e.g. bread, since they may be used at a relatively low level without loss of taste in the foodstuff. Other uses of the salt products of the invention are as carriers for pharmaceuticals.

Sodium chloride (hereinafter referred to simply as "salt" unless the context otherwise requires) has been used since time immemorial for the seasoning/flavouring of food since it is generally felt that food without salt lacks taste. Large amounts of salt are used, for example, by the food manufacturing industry in the production of pre-prepared foods, for example bread, ready meals, sauces, cured meats, sausages, burgers and crumbed products. Salt is of course also used in home cooking and is also sprinkled on prepared food as a condiment.

It is however become clear over recent years that too much salt in the diet can give rise to adverse health consequences, e.g. high blood pressure which is a risk factor for stroke. To put the problem into perspective, UK Government figures indicate that the average intake of salt per person is approximately 6.0-9.0 grams per day. However the UK Government recommended maximum is 3 grams per day. Clearly therefore some reduction in the current salt content of at least pre-prepared foodstuffs is a desirable goal.

One pre-prepared foodstuff which has come in for criticism in terms of its high salt content is bread. In the UK, bread supplied by supermarkets and other stores generally contains 1.8% to 2.0% by weight of salt. The UK Food Standards Agency has a target for the salt level in bread to be reduced to 1.1%.

In principle, one way of reducing the amount of salt in a food product would be to mill the salt to give a very large surface area which should mean that the same "seasoning level" may be achieved using a lower amount of salt. However salt is hygroscopic and the finely milled product quickly re-agglomerates unless protected using expensive or complex storage systems which would add additional cost to what is otherwise a commodity product.

A further possibility is to replace at least a portion of the salt with a substitute therefor. Alternatives to sodium chloride include the use of magnesium and potassium chlorides but these impart a bitter or metallic taste which is not generally acceptable to consumers. Furthermore the use of potassium and magnesium ions also affects neurons and can lead to changes in blood pressure. Other substitutes include organic molecules, such as monosodium glutamate (MSG), peptides and nucleic acid based substitutes. However these have their own problems. Thus, for example, there is a reported cancer risk associated with MSG. Additionally the substitutes may affect texture of the final finished food product and may have a potential to induce allergic responses. As a consequence, salt substitutes have replaced one "problem" with other issues and as a consequence are finding resistance within the food manufacturers sector and among public driven pressure groups.

Not only are there disadvantages with the use of substitutes but there can also be disadvantages associated with reduction of salt levels in the case of bread, particularly if the salt level is reduced below 1%, namely;

1. Loss of control over the fermentation
2. Loss of bread structure (irregular wholes-crumb structure)
3. Decreased bread height
4. Reduced shelf life as a result of reduced water content.

It is an object of the present invention to obviate or mitigate the above mentioned disadvantages.

According to a first aspect of the present invention there is provided a method of preparing a salt product comprising the steps of:

(i) providing a mixture which comprises salt dissolved in a solvent, said mixture further containing an organic material that is solid under ambient temperature conditions; and (ii) atomising said mixture and evaporating said solvent to produce a salt product comprised of particles of salt incorporating said organic material.

We have found in accordance with the invention that it is possible to produce a salt product with highly advantageous properties (detailed below) by atomising a mixture which comprises a solution of salt (sodium chloride) in a solvent (most preferably water) and which further contains an organic material that is a solid at ambient temperature to produce atomised droplets under conditions in which the solvent is evaporated from the droplets to leave a particulate product which is comprised of salt and the organic material. The particles of the product may have a particle size less than 100 microns but in spite of this very small size it is found that the salt product is essentially non-hygroscopic and is capable of remaining as a free-flowing solid that can be stored under ambient conditions (e.g. in bags or other containers) without special precautions yet still remain free-flowing for time periods in excess of 18 months, e.g. when stored at 15-25° C. with a relative humidity of 70%. A primary use of the salt product produced in accordance with the invention is as a seasoning in the manufacture of food, for which purpose the salt product will be produced with an organic material acceptable for alimentary use. Weight-for-weight, the salt product produced in accordance with the invention has enhanced "saltiness" as compared to conventional salt and may be used in much lower amounts in food whilst still providing the same taste level. Very surprisingly we have found that the salt product produced in accordance with the invention may be used in the manufacture of bread products at much lower levels than conventional salt whilst still being capable of providing the same taste and without adversely affecting the bread production process.

The salt product produced by the method of the invention may have a particle size such that substantially all (more than 95%) of the particles have a size less than 100 µm. Substantially all of the particles may have a size in the range 2 µm-100 µm. The salt product may be such that more than 95% of the particles have a size less than 50 µm.

Preferred products produced in accordance with the method of the invention comprise a substantial proportion of particles having a structure comprised of individual crystallites salt attached together in the particle. We believe it is the presence of the organic material that maintains the coherency of these particles. Particularly preferred products produced by the method of the invention have a substantial proportion of the particles that are hollow and are formed of an outer shell of the crystallites. The structure of such salt products is to our knowledge unique. When seen under a Scanning Electron Microscope at an appropriate magnification (e.g. ×5000) preferred embodiments of salt product in accordance with the invention have individual particles that are seen to be generally spheroidal (although not necessarily spherical in the truest geometric sense) and are of a hollow structure in which the shell is comprised of small generally rectangular crystallites of sodium chloride.

As summarized above, the salt product in accordance with the invention is prepared from a mixture which comprises a solution of sodium chloride (preferably an aqueous solution) and which further contains an organic material that is per se a solid under ambient temperature conditions. The material should be a solid in the temperature range 15° to 35° C., more preferably 15° to 25° C., although it will be appreciated it may also be solid at a temperature outside these ranges. The organic material is preferably one which is soluble in the solvent. It is particularly preferred that the mixture to be atomised is a homogeneous solution. Any insoluble material in the mixture may be removed by conventional techniques, e.g. centrifugation, filtration etc.

To produce the salt product, the mixture is atomised under conditions providing for evaporation of the solvent from the atomised droplets to produce a particulate salt product as described above. An elevated temperature (e.g. 100° C. to 210° C.) may be used for evaporation of the solvent. The evaporation may be effected using a hot air cyclone effect. For the purposes of obtaining the preferred products of the invention, different temperature values may be appropriate for different organic materials. Specific temperatures are given below for maltodextrin (195° C.) and Gum Arabic (140° C.). The best value may be determined by simple experiment and is well within the capability of the person skilled in the art.

The atomisation and evaporation step may be effected using a conventional spray drying apparatus. For the purposes of small batches of the product, a Buchi Mini Spray Dryer B-290 is suitable. Nairo industrial driers may be used for commercial production of the product.

The mixture that is subjected to atomisation preferably contains 5% to 35% by weight salt based on the weight of the solvent, more preferably 10% to 35% and even more preferably 25% to 35% on the same basis. Alternatively or additionally the mixture preferably contains 0.1% to 20% by weight of the organic material based on the weight of the solvent, more preferably 0.3% to 7% on the same basis.

If the salt product of the invention is being prepared for use in seasoning food then the sodium chloride should be of food grade quality.

The organic material is preferably a polymeric material. A wide variety of such polymeric materials may be used to produce salt products in accordance with the invention, preferred polymeric materials being at least partially and ideally substantially soluble in the solvent. Therefore preferred polymers have substantial solubility in water, the preferred solvent for use in the invention. The polymer may be natural or synthetic although there is a constraint in that it should be a polymer which is acceptable for alimentary purposes.

Examples of natural polymers include carbohydrates and proteins. Mixtures of such polymer types may also be used. If the polymer is a carbohydrate then it may, for example, be one or more of maltodextrin (e.g. Fibresol), Gum Arabic, starch (e.g. soluble corn starch, potato starch or soya bean starch), Guar Gum, Carageenan, hydroxypropyl cellulose and agar. If maltodextrin is used then it may be one having a dextrose equivalent of 13.0-17.0. When maltodextrin is used it is preferably present in the mixture in an amount of 0.5% by weight based on the volume of the solvent. Evaporation of the solvent (when using maltodextrin) is preferably effected at a temperature of 190°-200° C., e.g. about 195° C. If Gum Arabic is used then it is preferably Acacia Gum. When used, Gum Arabic is preferably present in the mixture in an amount of about 3% by weight and evaporation is preferably effected at a temperature of 135 to 145° C., e.g. about 140° C./

A further example of natural polymer that may be used is Natto which is obtained by fermentation of soya beans using *Bacillus Subtilis*. This fermentation produces a "sticky product" on the surface of the beans. The beans may then be mixed with an equal volume of water and homogenised to produce Natto.

Examples of synthetic polymers that may be used include polyethylene glycol although this will is not suitable for food application. The polyethylene glycol may, for example, have a molecular weight in the range 3,000-20,000.

Although organic polymeric materials (that are solid at ambient temperature) are the preferred organic materials for use in formulating the mixture that is to be subjected to atomisation and spray drying, other organic materials may be used, e.g. fats such as plant or animal derived fats.

The organic material used in the production of the salt product can be selected to provide particular characteristics for the product. One characteristic that has been mentioned above is the selection of an organic material which is acceptable for alimentary use. It is however also possible to select the material to provide particular physical and/or chemical characteristics for the salt product, e.g. the hydrophilicity/hydrophobicity of the product. Thus, for example, the organic material may be one which is of a hydrophobic nature such as plant fat to provide for fat solubility characteristics of the salt product. Examples of materials that provide for such fat solubility are Trex, carrageenan and coconut butter. Alternatively the organic material may be one intended to provide hydrophilic characteristics e.g. maltodextrin, Fibersol and soluble starches. A further possibility is the use of a polymer which imparts resistance to degradation of the particles under particular pH conditions.

The salt product has a wide variety of uses, a number of which will be detailed below.

A significant use of the salt product is as a seasoning for food because, as indicated above, much lower amounts of the salt product may be used to obtain the same degree of seasoning as compared to the use of conventional salt. This enables a significant reduction in a person's salt intake to be achieved. For use in food applications, the organic polymer used for producing the salt product the organic polymer should be one that is acceptable for alimentary use and may (but not necessarily) be one which does not itself add any significant taste to the food product (i.e. the organic polymer is essentially "taste-neutral". Examples of organic polymers which meet these criteria include Gum Arabic (particularly Acacia Gum), maltodextrin, Guar Gum, Carrageenan, Hydroxypropyl cellulose and agar. Such salt products may generally be used in all applications where conventional salt is employed.

The salt product is especially (but not solely) useful in the manufacture of bread as a replacement for conventional salt. The salt product may be used at much lower levels that conventional salt (e.g. up to 70% less) whilst still providing the required degree of seasoning and without detriment to the bread manufacturing process or the nature of the final product. More particularly, we have found that the salt product does not result in any of the following:

(i) loss of control over fermentation;
(ii) loss of bread structure (e.g. by the formation of irregular hole-crumb structures);
(iii) decreased bread height; or
(iv) reduced shelf life as a result of reduced water content.

Since bread (and other bread products) provide a significant contribution to the daily salt intake of a human being these findings are of major significance and allow the production of bread using conventional techniques (without any modification) with the bread having a much reduced salt content.

The salt product may be used for the seasoning of other manufactured food products. One example is the manufacture of dishes which comprise a meat (red or white) and a sauce therefor. For such products we have found that the salt product of the invention may be used in amounts up to 50% less than conventional salt whilst maintaining both texture and flavours.

They salt has been used in vegetarian sausages at level of between 25-50% reduction on normal levels without loss of flavour. It has also been used in crumb as a result of crumbing bread produced with the salt, reducing salt levels by upto 70%.

Whilst the use of a taste-neutral polymer is appropriate for many food applications there are other instances where the polymer may, with advantage, impart a taste to the salt product. Thus, for example, the salt product may be prepared with an extract of a flavouring product. The flavouring product may be of animal or vegetable origin and include an organic polymer (e.g. carbohydrate and/or protein) which serves for formation of the salt product. This polymer may per se be the one which provides the flavouring. Alternatively the flavouring extract may comprise the polymer and a (separate) flavouring per se which becomes incorporated in the salt product. Examples of flavouring components include, for example, meat extracts (e.g. of bovine, porcine or ovine origin), fish extracts, vegetable extracts (e.g. onion, garlic), herb extracts (e.g. basil) as well as other flavouring extracts (e.g. chilli).

Whilst reference has been made in the previous paragraph to salt products in which the flavouring extract provides the polymer for forming the product, there is also the possibility of forming salt products with, say, a taste-neutral polymer (e.g. Gum Arabic) and incorporating at least one non-polymeric flavouring component in the mixture to be subjected to atomisation and evaporation, thereby obtaining a flavoured salt product.

Flavoured salt products of the types discussed in the preceding two paragraphs have advantages in that the salt and the flavouring required for manufacture of food product are provided in a single salt product with, of course, the advantage that a lower amount of salt is used in the food.

Flavoured salt products may, for example, be used in the manufacture of "snack-foods" (which may be cooked or uncooked). Thus, for example, a salt product incorporating chilli may be used in the manufacture of potato-based snack foods (e.g. crisps) to provide a flavoured product. It will however be understood that such snack foods (e.g. potato based) may be produced with salt products having flavourings other than chilli.

A further food application is the use of the salt product for the manufacture of a drink, such as a so-called 'energy drink'.

A still further application is as a delivery system for a pharmaceutical which is incorporated in the mixture that is subjected to atomisation and evaporation in step (ii) of the process. The salt product may be intended for oral administration, in which case the organic material used in formation of the product can be an enteric polymer such as polylactic acid which prevents dissolution of the particles at a pH of 2-4 to provide acid resistance, sugars (dextrose) to provide a measure of slow release. Standard pharmaceutical coatings can also be applied that provide transport across the stomach into the intestine.

The present invention will be illustrated with reference to the following non-limiting Examples and accompanying drawings, in which.

In the following Examples and Comparative Examples, the salt used was Sodium Chloride EP grade (Eur pH) from Fisher Scientific.

COMPARATIVE EXAMPLE 1

Figure 1:
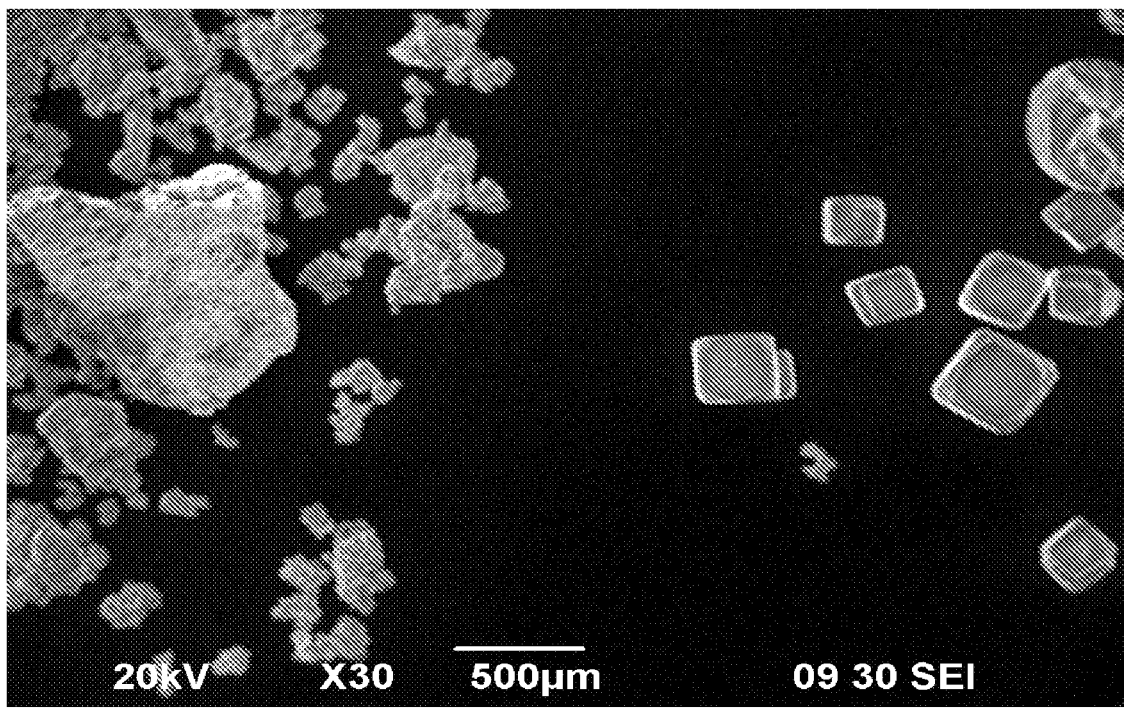
FIG. 1 is an SEM showing the results of COMPARATIVE EXAMPLE 1.

Salt was milled to a particle size of 50 μm. It was found that the milled particles rapidly formed agglomerates at ambient conditions. An SEM of the agglomerated product (×30 magnification) is shown at the left hand side of FIG. 1 which, for the purposes of comparison, also includes the unmilled salt crystals which display their normal rhomboid crystal form with a size ca 500 μm.

EXAMPLE 1

3 gms of Gum Arabic (Acacia Gum—ex Fluka) was added to a solution of 15 gm salt dissolved in 100 ml of deionised water in a container. A lid was placed on the container and the contents shaken until a clear homogenous solution was formed (alternatively a Silverson emulsifier could have been used to provide the homogeneous solution).

The solution was then spray dried using a Buchi Mini Spray Dryer-290 set with the following parameters:

| | |
|---|---|
| Aspirator % = | 100 |
| Pump % = | 30 |
| Air flow (mm) = | 40 |
| Nozzle Cleaner = | 3 times per minute |
| Temperature Setting = | 140° C. |

Figure 2:
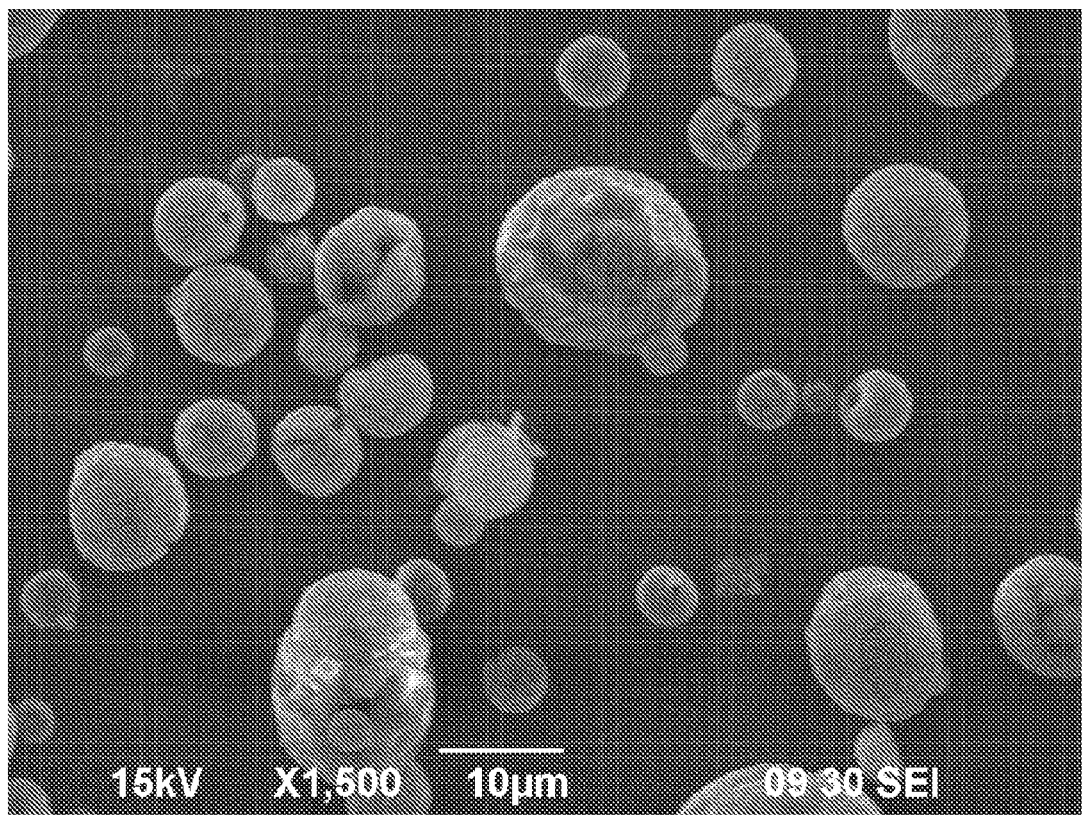
FIG. 2 is an SEM showing the results of Example 1.

This procedure resulted in a rapid recrystallisation of the solution producing a product for which the crystal structure is represented in the SEM of FIG. 2. As shown in this figure the salt product obtained comprise generally spherical particles (which contained both the salt and the Gum Arabic). These particles were hollow and their outer shell comprised individual crystallites of salt which are of generally square or rectangular appearance.

Significantly the salt product of Example 1 did not form agglomerates or clumps when stored under ambient conditions over a period of 18 months.

The salt product was fat insoluble and suitable for use as a seasoning in the manufacture of food products (see also Example 22 below).

COMPARATIVE EXAMPLE 2

The procedure of Example 1 was repeated but without the addition of the Gum Arabic to the salt solution.

Figure 3:
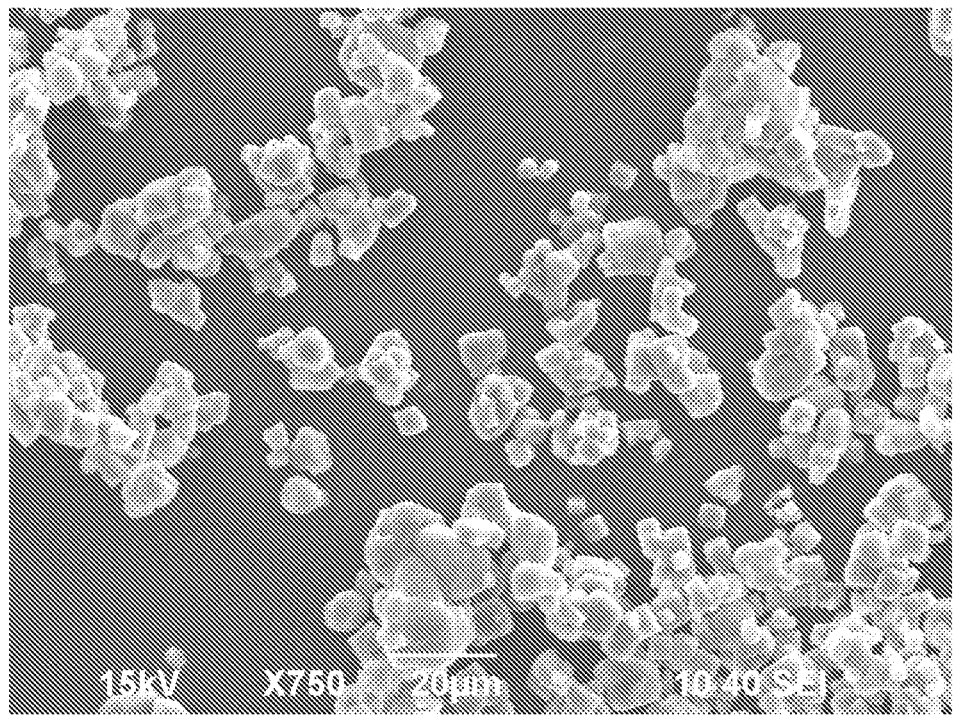
FIGS. 3 and 4 are SEMs showing the results of COMPARATIVE EXAMPLE 2.

An SEM of the product obtained is shown in FIG. 3 (×750 magnification). It can clearly be seen from FIG. 3 that salt obtained without the Gum Arabic does not form the "crystalline ball" structure obtained with the use of Gum Arabic and shown in FIG. 2.

Figure 4:
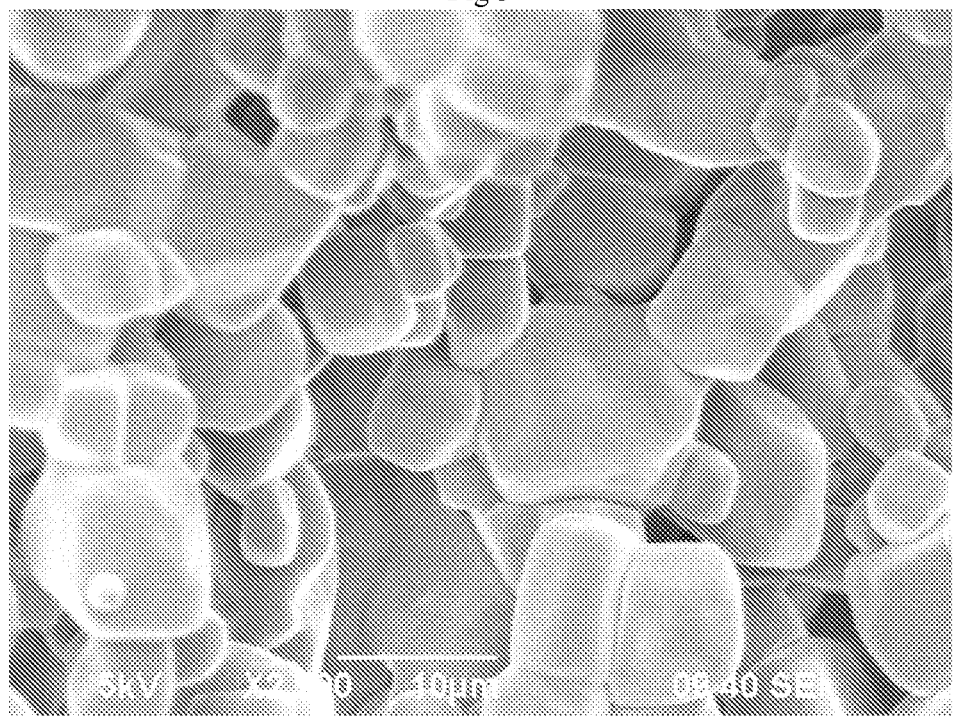

The product of COMPARATIVE EXAMPLE 1 rapidly formed aggregates and clumps under ambient conditions less than 1 hour after its production. The aggregated salt is shown in the SEM of FIG. 4 (×2000 magnification) which once again confirms the absence of the "crystalline ball" structure.

EXAMPLE 2

The procedure of Example 1 was repeated but using 30 gm salt and 2% Gum Arabic.

Figure 5:
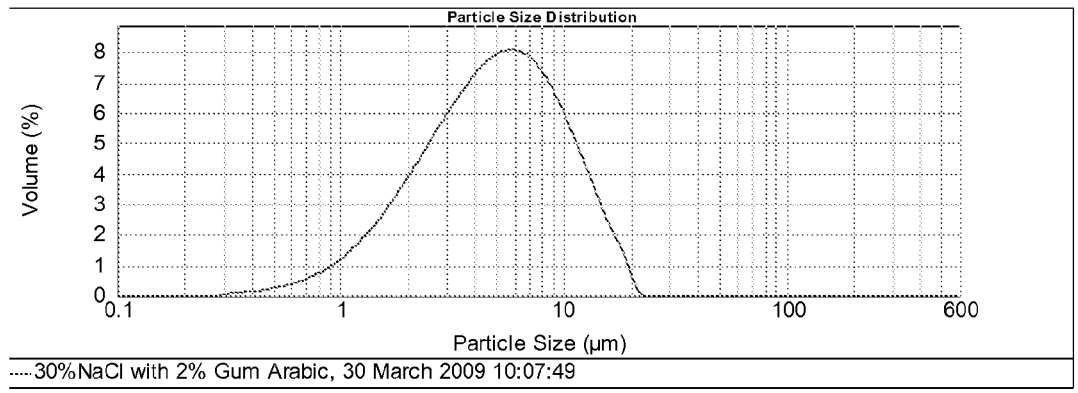
FIG. 5 shows a particle size distribution for the product obtained in accordance with Example 2.

The particle size distribution of the resultant product as obtained on a Mastersizer (Laser Light Scattering device) is shown in FIG. 5. It will be noted that all particles were below 30 μm in size.

The mean average particle size was determined to be 6-7 μm. The following additional data were determined:
Specific surface area 1.75 m2/g Surface weighted mean D [3, 2] 3.422 μm Vol. weighted mean D [4, 3] 5.939 μm.
d (0.1) 1.697 um d (0.5) 4.977 um d (0.9) 11.673 um
Where d (0.1) is the size of particle below which 10% of the sample lies
d (0.5) is the size of particle which 50% is smaller and 50% larger
d (0.9) is the size of particle below which 90% of the sample lies.

The product remained non-agglomerating under ambient conditions.

EXAMPLE 3

Example 2 was repeated but using a Nairo spray drying machine set with the same parameters (T=140° C.) as the Buchi Spray Dryer employed in Example 2.

Whereas the Buchi Spray Dryer is a laboratory scale apparatus, the Nairo apparatus was used in this Example to demonstrate the possibility of producing the salt product on an industrial scale.

Figure 6:
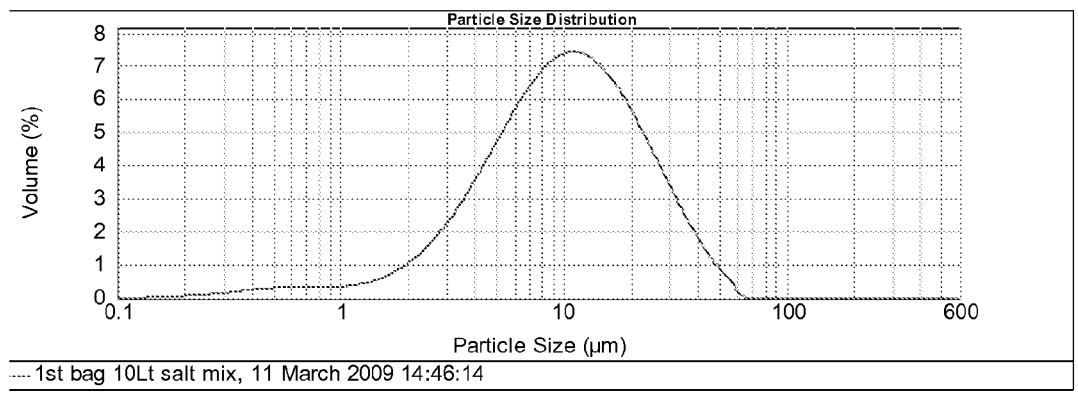
FIG. 6 shows the particle size distribution for the product obtained in accordance with Example 3.

The particle size distribution of the resultant product as obtained on a Mastersizer (Laser Light Scattering device) is shown in FIG. 6. It will be noted that all particles were below 100 μm in size.

The mean average particle size was determined to be 11-12 μm.

The following additional data were determined:
Specific surface area 1.12 m2/g Surface weighted mean D [3, 2] 5.337 μm Vol. weighted mean D [4, 3] 13.090 um
d (0.1) 3.175 um d (0.5) 10.248 um d (0.9) 27.161 um
Where d (0.1) is the size of particle below which 10% of the sample lies
d (0.5) is the size of particle which 50% is smaller and 50% larger
d (0.9) is the size of particle below which 90% of the sample lies.

EXAMPLE 4

0.5 gm of Maltodextrin having a dextrose equivalent of 13.0-17.0 (ex Sigma Aldrich) and 15 gm of salt were added to 100 ml of deionised water in a 180 ml polyethylene container. The lid was replaced and the contents shaken until a clear homogenous solution was formed. The solution was then spray dried in the Buchi Mini Spray Dryer B-290 using the same settings as in Example 1 but with the temperature set at 195° C.

Figure 7:
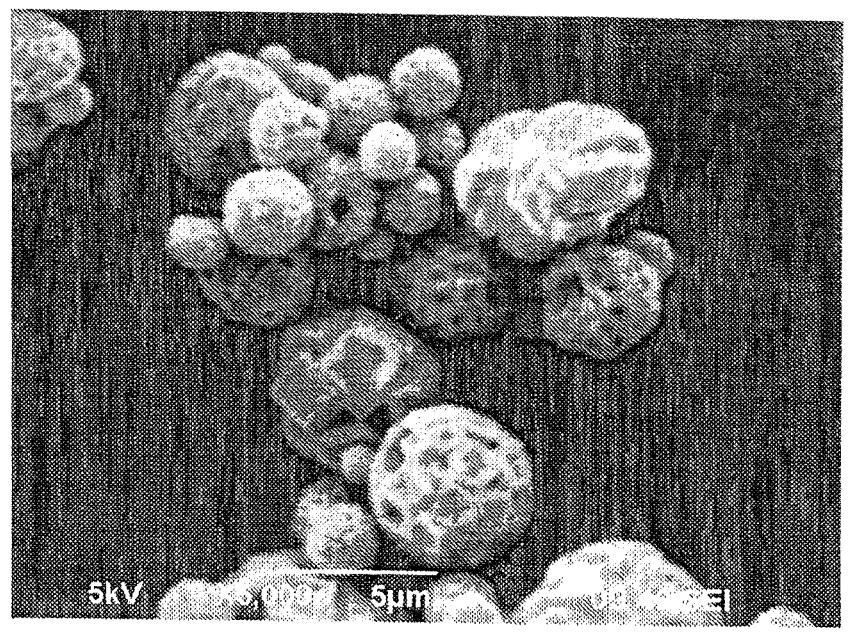
FIG. 7 is an SEM of the product obtained in accordance with Example 4.

An SEM (×5000) of the product is shown in FIG. 7. The particles will be seen to comprise hollow spheres having a shell formed of individual salt crystallites.

EXAMPLE 5

Figure 8:
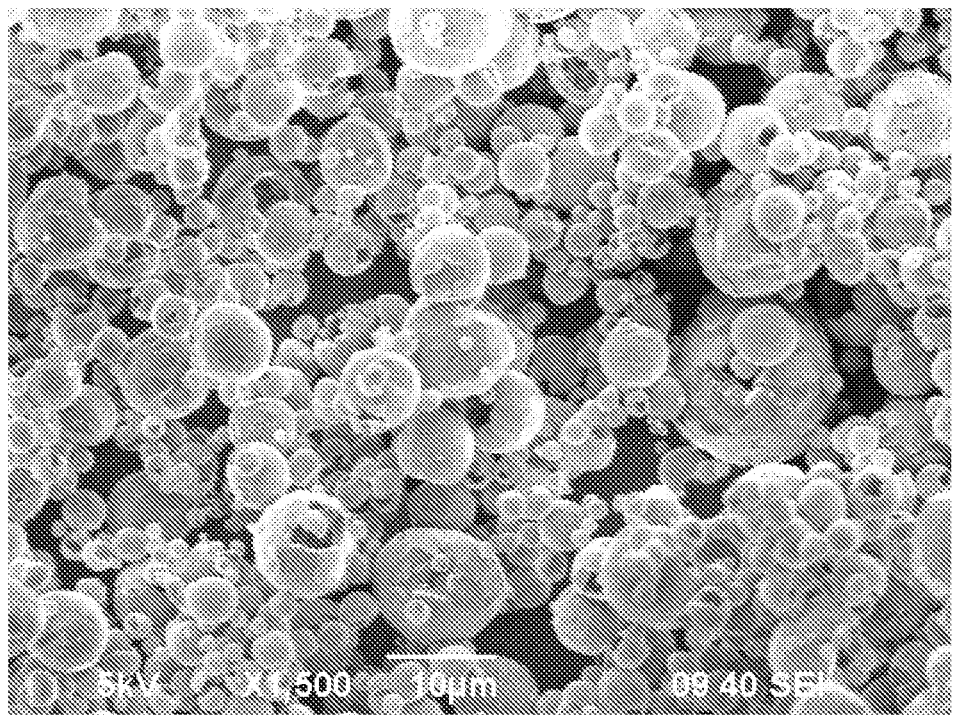
FIG. 8 is an SEM of the product obtained in accordance with Example 5.

To an aqueous solution of 15 gm of salt in 100 ml of deionised water was added 0.5 gm of maltodextrin having a dextrose equivalent of 13.0-17.0 (ex Sigma Aldrich) with mixing. To the resultant mixture was added 1.5 gm Aspirin and further mixing was effected using a Silverson emulsifier. The obtained mixture was then subjected to spray drying using a Buchi-Mini Spray Dryer-290 set with the same parameters as in Example 4. A particulate salt product was produced for which an SEM is shown in FIG. 8 (×1500 magnification). The particles produced had a size range of 1 nm-100 μm, the particles being generally spherical and hollow.

As seen in FIG. 8, the "salt balls" have a "smooth" appearance demonstrating that the Aspirin has been deposited as a coating on the outer surface of the balls since the individual crystallites which form the balls are not as visible as they are in FIG. 7 although some can be seen. It is possible to control the "coating thickness" by increasing the concentration of the Aspirin (data not presented).

EXAMPLE 6

To an aqueous solution of 15 gm of salt in 100 ml deionised water was added 0.5 gm of maltodextrin of the type used in Example 4. To this mixture of salt and maltodextrin was added 1.5 gm of garlic extract.

Mixing was effected with a Silverson emulsifier.

Figure 9:
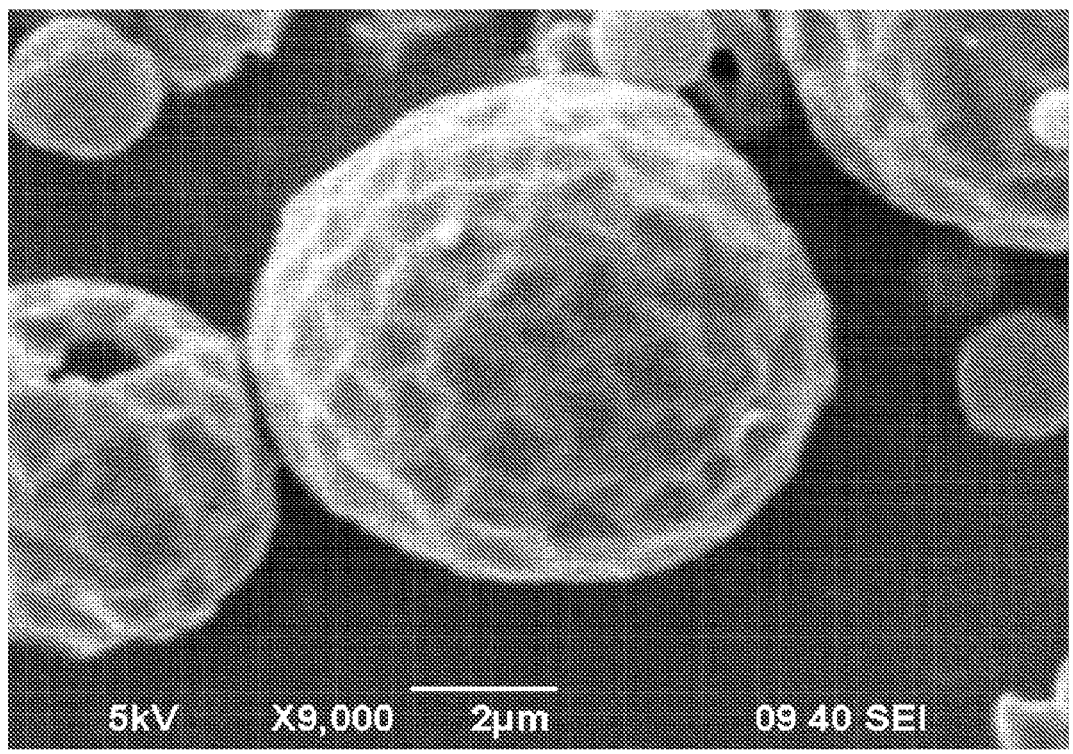
FIG. 9 is an SEM of the product obtained in accordance with Example 6.

The obtained solution was then subjected to spray drying using a Buchi Mini Spray Dryer-290 set with the same parameters as used in Example 4. An SEM for the product obtained is shown in FIG. 9 (×9000 magnification). The particles had a size in the range of 1 nm-100 μm with a mean of approximately 7 μm. The particles shown in FIG. 9 clearly demonstrate an altered crystal structure from the normal rhomboid crystal of table salt which has a crystal size of ca 500 μm (see SEM of FIG. 1) to a flat planar triangular form which clearly aids ball formation. As shown in FIG. 9 the size of these individual crystallites is ca 1 μm×0.5 μm.

EXAMPLE 7

15 gm of salt, 1 gm of Aspirin and 0.15 gm of Natto were added to 100 ml of deionised water in a 180 ml polyethylene container and sonicated for 15 minutes. The solution did not completely dissolve so it was then heated in a water bath at 37 degrees Centigrade.

The liquid was centrifuged on a Sigma 2-16 at 6183 rpm and 4060 g. Subsequently the supernatant liquid was spray dried using a Buchi Mini Spray Dryer B-290 using the same settings as previously save that the temperature was 195° C.

A particulate salt product was obtained.

EXAMPLE 8

15 gm of salt, 1 gm of Caffeine and 1 gm of Natto were added to 100 ml of deionised water in a 180 ml polyethylene container. The lid was replaced and the contents shaken. The solution was centrifuged on a Sigma 2-16 at 1683 rpm and 4060 g for 14 minutes. The supernatant liquid was then spray dried at 195° C. on a Buchi Mini Spray Dryer B-290 using the same settings as in Example 7.

A particulate salt product was obtained.

EXAMPLE 9

To an aqueous solution of 15 gm of salt in 100 ml deionised water was added 3 gm of PEG having a molecular weight of 20,000. To this was added 10 g of Aspirin.

This solution was then subjected to spray drying using a Buchi Mini Spray Dryer B-290 with the same settings as previously but a temperature of 140° C. with the production of capsules in the size range of 1 µm-100 µm.

EXAMPLE 10

This Example demonstrates production of a flavouring additive based on Basil.

Basil leaves were prepared for extraction by firstly crushing them by hand, then mixing them with a hand held blender and finally crushing with a pestle and mortar. The Basil was extracted overnight with 10% Ethanol 96% v/v and 90% deionised water using a FT 110 Rapid Extractor with the following settings.

| | |
|---|---|
| TP0 = | 1: 30 |
| TP1 = | 2: 00 |
| Cycles = | 35 |
| PMax = | 9 |
| PMin = | 6 |

The Basil extract was then centrifuged at 6461 g for 15 minutes and the supernatant liquid further treated as follows 30 gm of salt and 12 gm of 3000PEG were added to 100 ml of deionised water in a 250 ml glass beaker. The beaker was placed on a Corning Stirrer/Hotplate and a magnetic flea added. The solution was agitated at 55° C. until a clear colourless liquid was formed.

75 ml of the Basil extract was added to a 180 ml polyethylene container and 25 ml of deionised water added. The lid was replaced and the contents shaken until a homogenous solution was formed. 100 ml of the Basil extract was added to the beaker containing the PEG solution and the solution agitated until a homogenous solution was formed. The solution was spray dried using a Buchi Mini Spray Dryer B-290 using a temperature setting of 140° C. with the other settings being as previously.

A particulate salt product incorporating the Basil flavour was obtained.

EXAMPLE 11

2 Vegetable stock cubes each having a weight of about 11.2 gm and 15 gm of salt were added to 100 ml of deionised water in a 180 ml polyethylene container. The lid was replaced and the contents shaken until dissolved. The solution was then spray dried on a Buchi Mini Spray Dryer B-290 using a temperature setting of 140° C. with the other settings as previously.

The product was a white crystalline free flowing salt with a high flavour impact of vegetable stock.

EXAMPLE 12

15 gm of salt and 0.15 gm of Natto were added to 100 ml of deionised water in a 180 ml polyethylene container. The mixture was subjected to high shear force with a Silverson emulsifier and subsequently centrifuged for 14 minutes on a Sigma 2-16 at 4060 g. The resulting supernatant was then spray dried on a Buchi Mini Spray Dryer B-290 using a temperature setting of 195° C. with the other settings being as previously.

The product was a white crystalline free flowing salt with a high flavour impact of Natto but without the typical odour of Natto.

EXAMPLE 13

15 gm of salt with 0.5 gm of Maltodextrin (as used in Example 4 was added to 100 ml of deionised water in a 180 ml polyethylene container. The lid was replaced and the contents shaken until a clear colourless solution was formed. 8 gm Natural Chocolate Flavor Prod 013161 (Carmi Flavors) was added to the container and the contents shaken until a clear homogenous brown solution was formed. The solution was then spray dried on a Buchi Mini Spray Dryer B-290 using a temperature setting of 195° C. with the other settings as previously.

The resulting product contained capsules of product in the size range 1-100 µm the powder was free flowing and dark brown. The flavour was that of strong chocolate.

EXAMPLE 14

This Example demonstrates production of a water insoluble form of a salt product in accordance with the present invention.

15 gm of salt, 0.1 gm of Boric Acid and 0.5 gm of Maltodextrin (as used in Example 4) were added to 100 ml of deionised water in a 180 ml polyethylene container. The lid was replaced and the contents shaken until dissolved.

5 gm of Vegetable Fat (Terex) was added to a 250 ml glass beaker which was placed on a hotplate and heated until the vegetable fat melted. 10 ml of Ethanol (96% v/v) was added to the Vegetable Fat whilst still hot. Then 90 ml of the solution from the polyethylene container was added to the beaker and the contents thereof then mixed using a Silverston L4R at speed 2. Whilst still mixing the solution was spray dried on the Buchi Mini Spray Dryer B-290 using a temperature setting of 195° C. with the other settings as previously (to form a water insoluble salt suitable for use on snacks and in addition bread making.

The resulting white powder remained free flowing with high salt impact for at least 18 months.

EXAMPLE 15

A whole fresh onion was prepared for extraction by crushing with a jug blender. Then the onion was extracted with 10% Ethanol (96% v/v) and 90% deionised water using a FT 110 Rapid Extractor with the following settings.

| | |
|---|---|
| TP0 = | 1: 30 |
| TP1 = | 2: 00 |
| Cycles = | 35 |
| PMax = | 9 |
| PMin = | 6 |

30 gm of salt and 12 gm of 3000PEG was added to 100 ml of deionised water in a 250 ml glass beaker. The beaker was placed on to a Corning Stirrer/Hotplate and a magnetic flea added. The solution was agitated until a clear colourless liquid was formed. 100 ml of the onion extract was then added to the salt solution and the mixture subjected to high shear force (Silverson emulsifier) to produce a homogenous solution. The solution was spray dried in the Buchi Mini Spray Dryer B-290 using a temperature of 140° C. The product produced microcrystalline balls with the onion extract on the inside of the balls.

It was found with this and other formulations that if the salt was added to the onion extract then smooth balls where produced with the flavour on the exterior of the balls.

EXAMPLE 16

Turmeric was extracted overnight with a solution of 10% Ethanol (96% v/v) and 90% deionised water using a FT 110 Rapid Extractor with the following settings.

| | |
|---|---|
| TP0 = | 1: 30 |
| TP1 = | 2: 00 |
| Cycles = | 35 |
| PMax = | 9 |
| PMin = | 6 |

15 gm of NaCl EP grade was added to 100 ml of deionised water in a 180 ml polyethylene container. The lid was replaced and the contents shaken until a clear colourless solution was formed. Then 50 ml of this solution was added to another 180 ml polyethylene container and 50 ml of the Herb extract added. The lid was replaced and the contents shaken until a homogenous solution was formed. This solution was then spray dried on the Buchi Mini Spray Dryer B-290 using a temperature of 140° C. (other settings as previously).

The resulting product was a white powder formed with the aid of the organic polymers in the tumeric. Addition of water to the powder resulted in a bright yellow solution indicating that the turmeric was entrapped within the balls.

EXAMPLE 17

2 Beef stock cubes each having a weight of about 11.2 gm and 15 gm of NaCl were added to 100 ml of deionised water in a 180 ml polyethylene container. The lid was replaced and the contents shaken until dissolved. The solution was then spray dried on the Buchi Mini Spray Dryer B-290 using a temperature of 140° C. (same settings as previously). This resulted in smooth balls of high flavour intensity

EXAMPLE 18

2 gm of Lysozyme and 30 gm of NaCl were added to 200 ml of deionised water in a 250 ml glass beaker and a magnetic flea added. The beaker was placed on a Corning/Stirrer hotplate and the contents agitated until solids dissolved. Then 20 gm of Natto were added and the solution agitated for 30 minutes. The solution was then centrifuged on a Sigma 2-16 at 4060 g for 14 minutes. The supernatant liquid was collected. The solution was spray dried using a Buchi Mini Spray Dryer B-290 with a temperature setting of 195° C. and the other settings previously.

A particulate salt product was obtained.

Separate tests showed that the Lysozyme that had been incorporated in the product retained its activity.

EXAMPLE 19

15 gm of salt and 0.5 gm Maltodextrin were added to 100 ml of deionised water in a 180 ml polyethylene container. The lid was replaced and the contents shaken until a clear colourless solution was formed. 5 gm of Ground Cinnamon (Green Cuisine) were added and the lid replaced and the contents shaken. The Cinnamon was partially dissolved and suspended in solution so a magnetic flea was added and the container placed on the Corning/Stirrer Hotplate and the solution agitated for 30 minutes. The solution was then centrifuged on the Sigma 2-16 for 14 minutes at 4060 g. The cleared supernatant liquid was then spray dried in the Buchi Mini Spray Dryer B-290 using a temperature setting of 195° C. with the others settings as previously.

Figure 10:
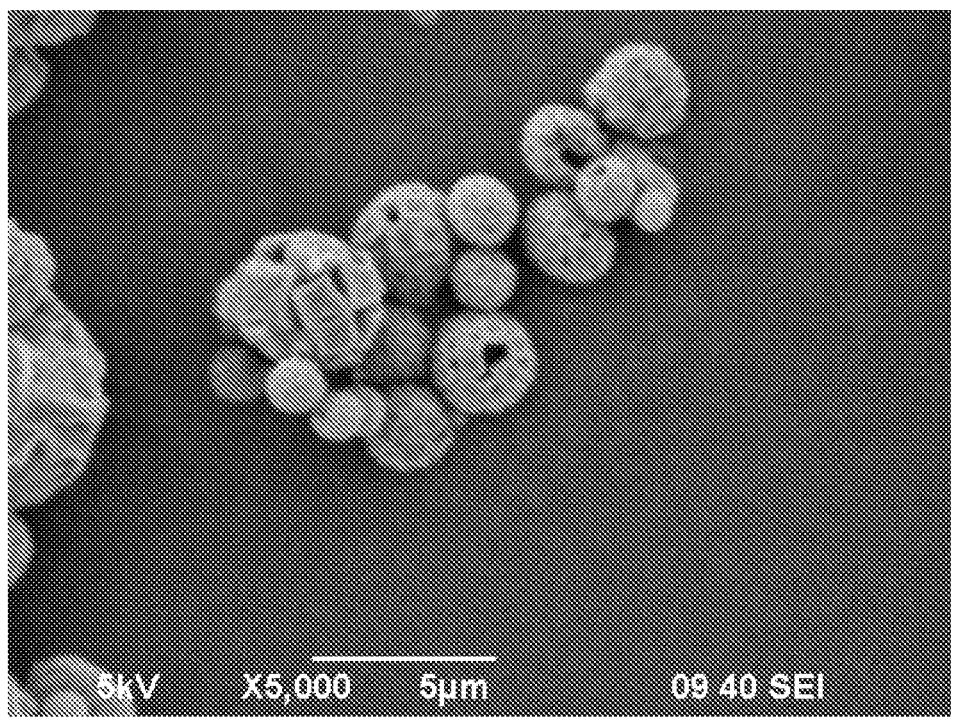
FIG. 10 is an SEM of the product obtained in accordance with Example 19.

The resulting product was a white crystalline powder with characteristic odour. The product is shown in the SEM of FIG. 10. In this SEM the product is seen to be made up of hollow "salt balls" for which the shell can be seen to be formed of individual crystallites indicating that the cinnamon has been included within the crystal ball.

EXAMPLE 20

This Example demonstrates the use of the Gum Arabic Salt product ("GA salt") obtained in accordance with Example 1 above in the baking of bread.

Four breads were prepared from the following component using standard procedures:

| | Control (1.3% salt) | GA salt (0.5%) | GA salt (0.3%) | GA salt (1.3%) |
|---|---|---|---|---|
| Flour | 380 g | 380 g | 380 g | 380 g |
| Improver | 40 g | 40 g | 40 g | 40 g |
| Yeast | ¾ tsp | ¾ tsp | ¾ tsp | ¾ tsp |
| Sugar | 1 tsp | 1 tsp | 1 tsp | 1 tsp |
| Butter | 15 g | 15 g | 15 g | 15 g |
| Salt | 5.6 g | 2.1 g | 1.26 g | 5.6 g |
| Water | 270 ml | 270 ml | 270 ml | 270 ml |

Following baking various parameters as shown in Table 1 were determined.

TABLE 1

| Product weight | Product | % Humidity | Bread height | Crumb structure | Texture | Flavour |
|---|---|---|---|---|---|---|
| 2.025 Kg | Normal Salt 1.3% | 43.81 | 14.00 cm | Good | Good | Salty |
| 2.025 Kg | GA 1.3% | 45.13 | 13.5 cm | Good | Good | Very salty |
| 2.025 Kg | GA 0.5% | 44.13 | 14.0 cm | Good | Good | Good |
| 2.025 Kg | GA 0.3% | 45.3% | 16.0 cm | Good | Good | Good |

The percent humidity (representing water retention in the bread) was determined for the four breads and found to be as shown in Table 2.

TABLE 2

| Product | % Humidity Day1 | % Humidity Day2 | % Humidity Day3 |
|---|---|---|---|
| Normal salt | 43.82% | 40.1% | 36.2% |
| GA 1.3% | 45.13% | 44.1% | 40.7% |
| GA 0.5% | 44.13% | 43.2% | 38.4% |
| GA 0.3% | 45.3% | 44.1% | 39.8% |

From these results bread prepared using 0.3% salt produced a very acceptable loaf that demonstrated water retention in the product that is important for shelf life and maintenance of "freshness". The fact that a very acceptable loaf was obtained using only 0.3% salt is surprising given the relatively high levels of conventional salt that are generally considered to be required for satisfactory bread production.

Figure 11:
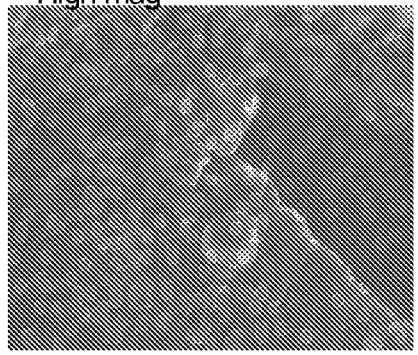
FIG. 11 shows EDX data for bread produced in accordance with Example 20.
Figure 11:
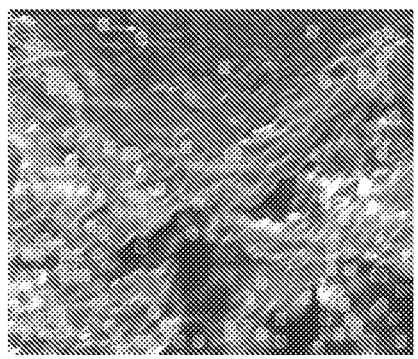

In an attempt to gain a better understanding of the process we undertook a more detailed analysis of the baked bread using Energy Dispersion X-Ray analysis which is capable of detecting the locations of specific ions. The results are shown in FIG. 11 for which the "dots" represent individual ions. The upper photograph (FIG. 11(a)) shows the result obtained for bread made with the GA salt and the lower photograph (FIG. 11(b)) shows the result for bread made with normal salt.

From the photographs of FIGS. 11(a) and (b) it can be seen that the GA salt is far more evenly distributed through out the bread. This we believe results in a better flavour impact at low salt concentrations and also aid in stabilising the gluten, prior to baking, by being more available for cross-linking the structure.

The invention claimed is:

1. A salt product comprising particles containing: i) salt and ii) a polymeric organic material selected from the group consisting of a carbohydrate, protein and synthetic organic polymer, said polymeric organic material being a solid at ambient temperature, said particles of said salt product having a structure comprised of individual crystallites of sodium chloride attached together in the particle, which particles of said salt product comprise hollow particles formed of an outer shell of said crystallites, wherein more than 95% of said particles of said salt product have a size less than 50 µm.

2. The salt product as claimed in claim 1 wherein said particles of said salt product are generally spheroidal and said outer shell is comprised of generally rectangular crystallites of sodium chloride.

3. The salt product as claimed in claim 1 wherein the polymeric organic material comprises at least one carbohydrate selected from the group consisting of maltodextrin, Gum Arabic, starch, Carrageenan, Hydroxypropyl cellulose and agar agar.

4. The salt product as claimed in claim 3 wherein the carbohydrate is Gum Arabic.

5. The salt product as claimed in claim 3 wherein the carbohydrate is maltodextrin.

6. The salt product as claimed in claim 5 wherein the maltodextrin has a dextrose equivalent of 13.0-17.0.

7. The salt product as claimed in claim 1 wherein the polymeric organic material comprises a synthetic organic polymer which is poly(ethylene glycol).

8. The salt product as claimed in claim 1 wherein said salt product comprises at least one additive.

9. The salt product as claimed in claim 8 wherein the additive is a flavour, pharmaceutical or fat.

10. The salt product as claimed in claim 1 wherein said polymeric organic material is acceptable for alimentary use.

11. A foodstuff seasoned with the salt product as claimed in claim 10.

12. The foodstuff as claimed in claim 11 wherein said foodstuff is a bread, a meat product, fish product or sauce.

13. The foodstuff as claimed in claim 11 wherein said foodstuff is a snack food.

14. The foodstuff as claimed in claim 11 wherein said foodstuff is a drink.

15. A method of seasoning a foodstuff with salt comprising adding the salt product as claimed in claim 10 to said foodstuff.

16. A method of producing a foodstuff comprising preparing a precursor of the foodstuff, said precursor incorporating the salt product of claim 10, and cooking said precursor to produce the foodstuff.

17. A method of preparing a bread product comprising the steps of:
(a) preparing a dough incorporating the salt product as claimed in claim 10; and
(b) cooking the dough to produce the bread product.

18. The salt product as claimed in claim 1 wherein said polymeric organic material is pharmaceutically acceptable.

19. The salt product as claimed in claim 18 wherein said salt product incorporates a pharmaceutical.

20. The salt product according to claim 1 wherein a substantial proportion of said particles of said salt product are hollow.

21. A method of preparing a salt product comprising the steps of:
(i) providing a mixture which comprises salt and a polymeric organic material dissolved in a solvent, wherein said polymeric organic material is selected from the group consisting of a carbohydrate, protein and synthetic organic polymer, said polymeric organic material being a solid under ambient temperature conditions; and
(ii) atomising said mixture to produce atomised droplets of the mixture and evaporating said solvent from the atomised droplets to produce a salt product which comprises particles containing: i) salt and ii) the polymeric organic material, said particles of said salt product having a structure comprised of individual crystallites of sodium chloride attached together in the particle, which particles of said salt product comprise hollow particles formed of an outer shell of said crystallites, wherein more than 95% of the particles have a size less than 50 µm.

* * * * *